(12) United States Patent
Raederstorff et al.

(10) Patent No.: US 8,158,681 B2
(45) Date of Patent: Apr. 17, 2012

(54) NUTRACEUTICAL AND PHARMACEUTICAL COMPOSITIONS AND USE THEREOF FOR THE TREATMENT, CO-TREATMENT OR PREVENTION OF INFLAMMATORY DISORDERS

(75) Inventors: Daniel Raederstorff, Flaxlanden (FR); Joseph Schwager, Basel (CH); Goede Schueler, Eimeldingen (DE)

(73) Assignee: DSM IP Assets B.V., Heerlen (NL)

( * ) Notice: Subject to any disclaimer, the term of this patent is extended or adjusted under 35 U.S.C. 154(b) by 146 days.

(21) Appl. No.: 12/279,510

(22) PCT Filed: Feb. 13, 2007

(86) PCT No.: PCT/EP2007/001241
§ 371 (c)(1),
(2), (4) Date: Aug. 14, 2008

(87) PCT Pub. No.: WO2007/093387
PCT Pub. Date: Aug. 23, 2007

(65) Prior Publication Data
US 2008/0319071 A1    Dec. 25, 2008

(30) Foreign Application Priority Data
Feb. 16, 2006 (EP) ................................. 06003162

(51) Int. Cl.
*A61K 31/20* (2006.01)
*A61K 31/085* (2006.01)
*A61K 31/192* (2006.01)
*A61P 19/02* (2006.01)
*C07C 43/23* (2006.01)
*C07C 65/28* (2006.01)

(52) U.S. Cl. ........ 514/559; 514/568; 514/719; 562/475; 568/646

(58) Field of Classification Search .................. 514/559, 514/568, 719; 562/475; 568/646
See application file for complete search history.

(56) References Cited

U.S. PATENT DOCUMENTS
2002/0034555 A1    3/2002    Gelber et al.

FOREIGN PATENT DOCUMENTS
WO    02/13809    2/2002
WO    02/14252    2/2002

OTHER PUBLICATIONS

Cho (Inhibitor of tumor necrosis factor-α production in lipopolysaccharide-stimulated RAW264.7 cells from *Amorpha fruticosa*, Journal of Ethnopharmacology, vol. 70 (2000) pp. 127-133).*
Onwukaeme (Anti-inflammatory activities of flavonoids of *Baphia nitida* Lodd. (leguminosae) on mice and rats, Journal of Ethnopharmacology, vol. 46, (1995) pp. 121-124).*

(Continued)

*Primary Examiner* — Brandon Fetterolf
*Assistant Examiner* — Kathrien Cruz
(74) *Attorney, Agent, or Firm* — Nixon & Vanderhye P.C.

(57) ABSTRACT

The present invention relates to new methoxylated aromatic compounds. It also relates to novel compositions comprising methoxylated aromatic compounds as well as to the use of these compositions as a medicament, in particular as a medicament for the treatment, co-treatment or prevention of inflammatory disorders.

14 Claims, 1 Drawing Sheet

OTHER PUBLICATIONS

Bitkilerin et al (Antimicrobial activity of some plants used in Folk Medicine, Ankara Eca. Fak. Derg 32 (3) 2003, pp. 159-163).*

Mitcher (Amorfrutin A and B, Bibenzyl Antimicrobial agents from *Amorpha fruticosa*, Phytochemistry, vol. 20, No. 4 1981, pp. 781-785).*

Black (Oral Antimicrobial Therapy for Adults with Osteomyelitis or Septic Arthritis, The Journal of Infectious Disease, 1987 vol. 155, Vo 5, pp. 968-972).*

International Search Report for PCT/EP2007/001241, mailed May 15, 2007.

Written Opinion of the International Search Authority, mailed May 14, 2007.

Ghisalberti, E. L. et al., "Isoprenylated Resorcino Derivatives from Glycyrrhiza Acanthocarpa", Phytochemistry, vol. 20, No. 8, pp. 1959-1961, (1981).

* cited by examiner

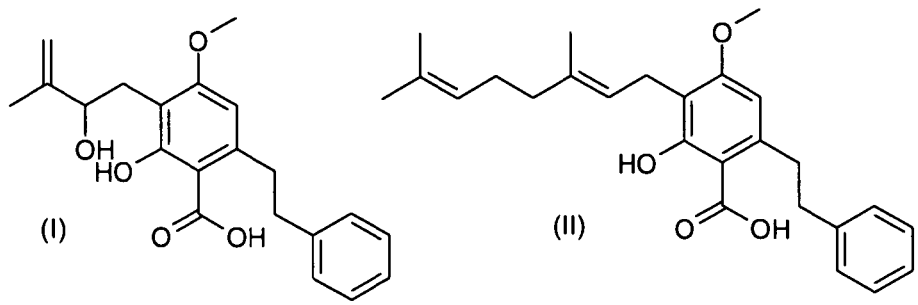
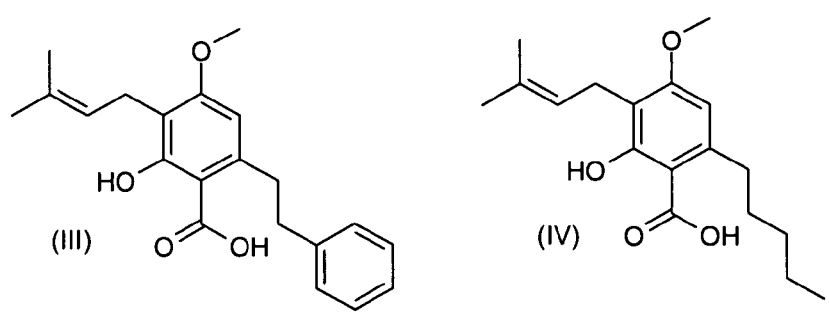
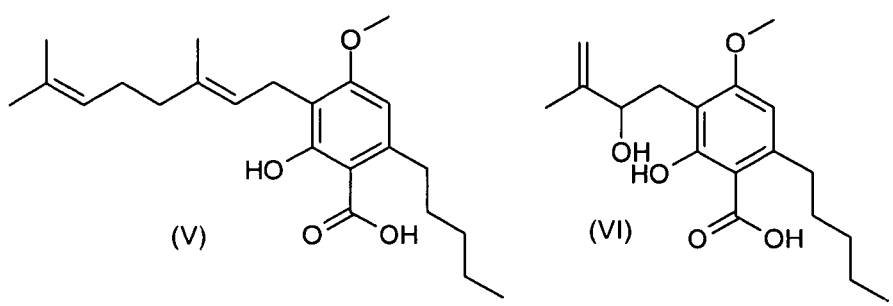
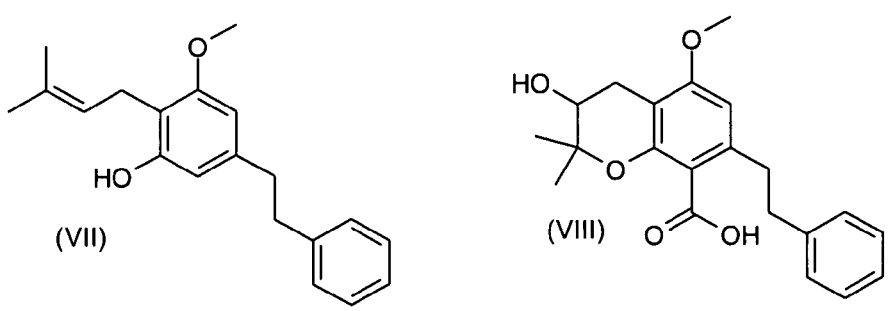
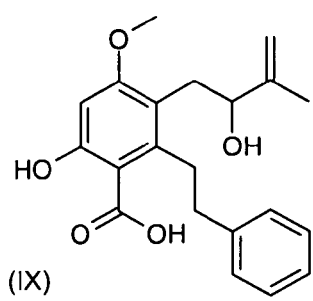

NUTRACEUTICAL AND PHARMACEUTICAL COMPOSITIONS AND USE THEREOF FOR THE TREATMENT, CO-TREATMENT OR PREVENTION OF INFLAMMATORY DISORDERS

This application is the U.S. national phase of International Application No. PCT/EP2007/001241, filed 13 Feb. 2007, which designated the U.S. and claims priority to Europe Application No. 06003162.2, filed 16 Feb. 2006, the entire contents of each of which are hereby incorporated by reference.

The present invention relates to new methoxylated aromatic compounds. It also relates to novel compositions comprising methoxylated aromatic compounds as well as to the use of these compositions as a medicament, in particular as a medicament for the treatment, co-treatment or prevention of inflammatory disorders.

Inflammatory disorders are one of the most important health problems in the world. Inflammation is in general a localized protective response of the body tissues to invasion of the host by foreign material or injurious stimuli. The causes of inflammation can be infectious agents such as bacteria, viruses, and parasites; or physical agents such as burns or radiation; or chemicals like toxins, drugs or industrial agents; or immunological reactions such as allergies and autoimmune responses or conditions associated with oxidative stress Inflammation is characterized by pain, redness, swelling, heat, and eventual loss of function of the affected area. These symptoms are the results of a complex series of interactions taking place between the cells of the immune system. The response of the cells results in an interacting network of several groups of inflammatory mediators: Proteins (e.g. cytokines, enzymes (e.g. proteases, peroxydase), major basic protein, adhesion molecules (ICAM, VCAM), lipid mediators (e.g. eicosanoids, prostaglandins, leukotrienes, platelet activating factor (PAF)), reactive oxygen species (e.g. hydroperoxides, superoxyde anion $O_2^-$, nitric oxide (NO) etc). However, many of those mediators of inflammation are also regulators of normal cellular activity. Thus, deficiencies of inflammatory reactions lead to a compromised host (i.e. infection) while uncontrolled and thus chronic inflammation leads to inflammatory diseases mediated in part by the excessive production of several of the above mentioned mediators.

Acute and chronic inflammation resulting from an excessive biosynthesis of inflammatory mediators is involved in numerous inflammatory disorders such as arthritis (e.g. osteoarthritis, rheumatoid arthritis), asthma, inflammatory bowel diseases, inflammatory diseases of the skin (e.g., psoriasis, eczema, atopic dermatitis) and chronic inflammatory disorders, such as atherosclerosis, heart diseases, metabolic syndrome X, cancer, Alzheimer's disease and pre-stages thereof such as mild cognitive impairment.

Rheumatoid arthritis is a chronic inflammatory disease of the joints. For example, arthritis includes rheumatoid arthritis, spondyloarthropathies, gouty arthritis, osteoarthritis, systemic lupus erythematosus and juvenile arthritis. Asthma and rheumatoid arthritis are characterised at the molecular level by chronically unbalanced expression of cytokines, chemokines, kinins and their receptors, adhesion molecules, and inflammatory enzymes.

Psoriasis is one of the most common skin problems, affecting 1-3% of the human population. Inflammatory bowel disease is a general term used to describe gastrointestinal tract diseases such as ulcerative colitis and Crohn's disease.

Beside the process of intravascular lipid deposition, inflammatory reactions of the endothelial (i.e. blood vessel) wall are considered to critically contribute to atherosclerosis i.e. atheroma formation. Atherosclerosis results from vascular injury which triggers inflammation. Activated macrophages, T-lymphocytes, and mast cells are present in atherosclerotic plaques. Monocyte/macrophage and lymphocyte activation leads to the release of eicosanoids and cytokines which are implicated in endothelial damage, as well as in the formation and eventually the rupture of atherosclerotic plaques. Finally, circulating inflammatory markers such as C-reactive protein (CRP), fibrinogen, and interleukins are increased in groups at high-risk of coronary artery diseases (CAD). Several clinical trials indicate that elevated CRP concentration correlates with increased risk of coronary, and vascular, events. Thus inflammation appears to play an important role in the initiation and progression of atheroma formation.

Inflammatory disorders are also associated with the pathophysiology of Alzheimer's disease. There is evidence of inflammation in the brain of patients with Alzheimer's disease, as it is characterized by increased levels of cytokines and activated microglial cells. Thus, inflammation is not only involved in the classical inflammatory disorders (e.g., arthritis, asthma, bowel diseases) but is also associated with many chronic inflammatory disorders (e.g., atherosclerosis, heart diseases, metabolic syndrome X, cancer, Alzheimer disease).

Inflammatory events are also associated with the pathophysiology of different types of cancers (e.g. gastric and intestinal cancers, melanomas). Increased levels of prostaglandins have been found in cancers of breast, colon, lung and pancreas in humans.

Two mains classes of drugs, the corticosteroid and the nonsteroidal anti-inflammatory drugs (NSAIDs) are used to treat inflammatory disorders. NSAIDs and corticosteroids provide essentially symptomatic relief. Use of corticosteroids has declined due to a growing concern about the serious side effects of prolonged use.

NSAIDs are among the most widely used drugs, primarily for the treatment of pain and inflammatory disorders, in particular for the treatment of arthritis. Epidemiological studies have suggested that patients taking NSAIDs have a lower risk of developing Alzheimer's disease than those not taking NSAIDs. A protective effect of NSAIDs suggests that the cyclooxygenases might be involved in the neurodegenerative process.

Epidemiological studies showed a significant reduction in the risk of colorectal, gastric, esophageal, and breast cancers among people who take non-steroidal anti-inflammatory drugs (NSAIDs) compared with those not taking NSAIDs. In animal models NSAIDs significantly reduced tumor development.

However, chronic use of NSAIDs when treating chronic diseases such as arthritis, is limited by severe side-effects like serious gastrointestinal complications, renal toxicity or asthmatic reactions.

Therefore, there is a need for new anti-inflammatory agents with weak or no side effects. Patients with inflammatory diseases have a special interest in treatment considered as "natural" with mild anti-inflammatory effects and without major side effects, which can be used for disease prevention and as adjuvant treatment.

It is the object of the present invention to address such need.

Thus, the invention relates to a composition comprising at least one methoxylated aromatic compound of formula (1)

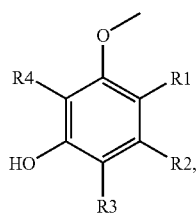

(1)

wherein
one of $R^1$ and $R^4$ stands for alkyl, alkenyl or for isoprenoid, preferably isoprenyl, geranyl or for 2-hydroxy-3-methyl-3-butenyl and the other one of $R^1$ and $R^4$ stands for H and
$R^2$ stands for H, or for an alkyl, preferably pentyl, or 2-phenylethyl and
$R^3$ stands for H or for a carboxyl group
or of formula (2)

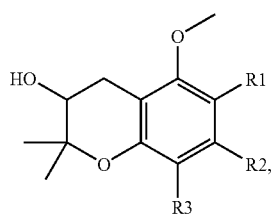

(2)

wherein $R^1$ stands for alkyl, alkenyl or for isoprenoid, preferably isoprenyl, geranyl or for 2-hydroxy-3-methyl-3-butenyl and
$R^2$ stands for H, or for an alkyl, preferably pentyl, or 2-phenylethyl and
$R^3$ stands for H or for a carboxyl group.

In a preferred embodiment, the at least one methoxylated aromatic compound is selected from the group of 2-hydroxy-4-methoxy-3-(2-hydroxy-3-methyl-3-butenyl)-6-(2-phenylethyl)-benzoic acid (I), Amorfrutin B (II), Amorfrutin A (III), 2-hydroxy-4-methoxy-3-(3-methyl-2-butenyl)-6-pentyl-benzoic acid (IV), Cannabigerolic acid monomethyl ether (V), 2-hydroxy-4-methoxy-3-(2-hydroxy-3-methyl-3-butenyl)-6-pentyl-benzoic acid (VI), 3-methoxy-2-(3-methyl-2-butenyl)-5-(2-phenylethyl)-phenol (VII), the compound of formula (VIII) and 2-hydroxy-4-methoxy-5-(2-hydroxy-3-methyl-3-butenyl)-6-(2-phenylethyl)-benzoic acid (IX). Compounds (I), (II), (III), (IV), (V), (VI), (VII), (VIII), and (IX) can be found in FIG. 1. Even more preferably, the methoxylated aromatic compound is selected from the group of cannabigerolic acid monomethyl ether (V), 2-hydroxy-4-methoxy-3-(2-hydroxy-3-methyl-3-butenyl)-6-pentyl-benzoic acid (VI), 3-methoxy-2-(3-methyl-2-butenyl)-5-(2-phenylethyl)-phenol (VII), in particular from 2-hydroxy-4-methoxy-3-(2-hydroxy-3-methyl-3-butenyl)-6-(2-phenylethyl)-benzoic acid (I), 2-hydroxy-4-methoxy-3-(2-hydroxy-3-methyl-3-butenyl)-6-pentyl-benzoic acid (VI), and the compound of formula (VIII).

The methoxylated aromatic compounds 2-hydroxy-4-methoxy-3-(2-hydroxy-3-methyl-3-butenyl)-6-(2-phenylethyl)-benzoic acid (I), 2-hydroxy-4-methoxy-3-(2-hydroxy-3-methyl-3-butenyl)-6-pentyl-benzoic acid (VI), and the compound of structure (VIII) are novel and form as such also part of the invention. These novel compounds can be isolated from a natural source and are for example obtainable from Glycyrrhiza foetida by methods known to a person skilled in the art.

It has surprisingly been found that the methoxylated aromatic compounds according to the invention are anti-inflammatory agents. Therefore, the compositions of the present invention may be especially useful in the treatment, co-treatment and prevention of inflammatory disorders, such as heart disease, multiple sclerosis, osteo- and rheumatoid arthritis, atherosclerosis, and osteoporosis.

The compositions of the present invention are especially suitable for the treatment, co-treatment and prevention of arthritis, in particular osteoarthritis and rheumatoid arthritis. Therefore, the compositions of the present invention may have one or more of the following properties: it reduces joint inflammation, it maintains and/or increases joint health, it prevents joint stiffness, it increases mobility, it provides supple and/or flexible joints, it lubricates the joints, it relieves arthritis pain, it relieves pain associated with joint inflammation, it decreases joint swelling, it lessens joint problems, it provides joint care.

The methoxylated aromatic compounds according to the invention may be synthesized or extracted and/or purified by methods known to the person skilled in the art. Preferably, the methoxylated aromatic compounds of the invention are derived from Glycyrrhiza foetida that may be obtained from conventional and commercially available sources such as growers.

The Glycyrrhiza foetida derived methoxylated aromatic compounds employed herein can be prepared by a number of methods known in the art. The Glycyrrhiza foetida may be processed by any suitable means to obtain the compositions described. For example, the Glycyrrhiza foetida may be extracted to obtain a mixture. The methoxylated aromatic compounds may be obtained directly from the mixture or the mixture may be fractionated and/or purified to obtain the methoxylated aromatic compounds. The compositions may be fractionated and/or purified by a number of methods known to the person skilled in the art. Examples of fractionating methods include partitioning with an organic solvent, chromatography, for example high pressure liquid chromatography (HPLC) or the use of supercritical fluids.

All compounds (I)-(IX) can be obtained by extraction of dried plant material of Glycyrrhiza foetida with methanol: MTB (9:1) and by subsequent fractionation of the thus obtained crude extract by preparative HPLC, for example in a buffered solvent system. Therefore, in another aspect, the invention relates to a process for the isolation of a compound of formula (1), (II), (III), (IV), (V), (VI), (VII), (VIII) and/or (IX), preferably a compound selected from the group of 2-hydroxy-4-methoxy-3-(2-hydroxy-3-methyl-3-butenyl)-6-(2-phenylethyl)-benzoic acid, 2-hydroxy-4-methoxy-3-(2-hydroxy-3-methyl-3-butenyl)-6-pentyl-benzoic acid (VI), 2-hydroxy-4-methoxy-3-(3-methyl-2-butenyl)-6-pentyl-benzoic acid and the compound of structure (VIII) by extraction of dried plant material of Glycyrrhiza foetida with an organic solvent, such as for example ethylacetate or a mixture of organic solvents, such as for example a mixture of an alcohol and an ether, preferably methanol and methyl-tert-butylether (MTB) and by subsequent fractionation of the thus obtained crude extract by preparative HPLC in a buffered solvent system.

The compositions of the invention expressly also encompasses an extract comprising a methoxylated compound according to the invention with the definitions and preferences as given above such as for instance a—preferably organic phase—extract of the plant material of Glycyrrhiza

*foetida*. Furthermore, the invention also encompasses compositions comprising the methoxylated aromatic compounds according to the invention with the definitions and preferences as given above in the form of an extract, in particular in the form of an extract obtainable from the plant material of *Glycyrrhiza foetida* such as for instance an organic phase extract.

The methoxylated aromatic compounds are preferably used in a concentration so that the daily consumption by a human adult (weighing about 70 kg) is in the range of from 0.5 mg/day to 2000 mg/day, preferably from 5 mg/day to 500 mg/day.

Therefore, the invention also relates to a composition comprising between 0.5 mg and 3000 mg, preferably between 1 and 2000 mg, more preferably between 1 and 1000 mg of methoxylated aromatic compound according to the invention with the definitions and preferences as given above.

In a different aspect, the invention also relates to a composition and/or a methoxylated aromatic compound, for use as a medicament. More in particular the invention relates to the use of this composition and/or a methoxylated aromatic compound for the manufacture of a nutraceutical or pharmaceutical composition for the treatment, co-treatment or prevention of inflammatory disorders, more preferably of arthritis, most preferably of rheumatoid arthritis or osteoarthritis.

Also, the invention relates to a method for treatment, co-treatment and prevention of inflammatory disorders, preferably of arthritis, most preferably of osteoarthritis, in animals including humans said method comprising the step of administering an effective amount of the methoxylated aromatic compound and/or composition according to the invention to animals including humans, which are in need thereof.

In the framework of the invention, with animals is meant all animals, including mammals, examples of which include humans. Preferred examples of mammals beside humans are non-ruminant or ruminant animals including cats, dogs, dromedaries, camels, elephants, and horses.

In another aspect, the invention relates to use of a composition according to the invention and/or a methoxylated aromatic compound according to the invention, with the definitions and preferences as given above for the manufacture of a nutraceutical or pharmaceutical composition.

In yet another aspect, the invention relates to a composition according to the invention, which is a nutraceutical composition, in particular a food or beverage or a supplement composition for a food or beverage further comprising a nutraceutically acceptable carrier, in particular for the treatment, co-treatment or prevention of inflammatory disorders, more preferably of arthritis, most preferably of rheumatoid arthritis or osteoarthritis.

The term nutraceutical composition as used herein include food product, foodstuff, dietary supplement, nutritional supplement or a supplement composition for a food product or a foodstuff.

Thus, in another embodiment the present invention relates to a nutraceutical composition comprising at least one methoxylated aromatic compound according to the invention with the definitions and preferences as given above wherein the nutraceutical is a food product, foodstuff, dietary supplement, nutritional supplement or a supplement composition for a food product or a foodstuff preferably a dietary supplement, a nutritional supplement or a supplement composition for a food or a foodstuff, preferably a supplement, nutritional supplement or a supplement composition for a food product or a foodstuff.

In another preferred embodiment the present invention relates to a nutraceutical composition comprising a plant extract obtainable from *Glycyrrhiza foetida* which is a food product, foodstuff, dietary supplement, nutritional supplement or a supplement composition for a food product or a foodstuff preferably a dietary supplement, a nutritional supplement or a supplement composition for a food or a foodstuff, preferably a supplement, nutritional supplement or a supplement composition for a food product or a foodstuff.

As used herein, the term food product refers to any food or feed suitable for consumption by humans or animals. The food product may be a prepared and packaged food (e.g., mayonnaise, salad dressing, bread, or cheese food) or an animal feed (e.g., extruded and pelleted animal feed, coarse mixed feed or pet food composition). As used herein, the term foodstuff refers to any substance fit for human or animal consumption. The term dietary supplement refers to a small amount of a compound for supplementation of a human or animal diet packaged in single or multiple dose units. Dietary supplements do not generally provide significant amounts of calories but may contain other micronutrients (e.g., vitamins or minerals). The term nutritional supplement refers to a composition comprising a dietary supplement in combination with a source of calories. In some embodiments, nutritional supplements are meal replacements or supplements (e.g., nutrient or energy bars or nutrient beverages or concentrates).

Food products or foodstuffs are for example beverages such as non-alcoholic and alcoholic drinks as well as liquid preparation to be added to drinking water and liquid food, non-alcoholic drinks are for instance soft drinks, sport drinks, fruit juices, such as for example orange juice, apple juice and grapefruit juice; lemonades, teas, near-water drinks and milk and other dairy drinks such as for example yoghurt drinks, and diet drinks. In another embodiment food products or foodstuffs refer to solid or semi-solid foods comprising the composition according to the invention. These forms can include, but are not limited to baked goods such as cakes and cookies, puddings, dairy products, confections, snack foods, or frozen confections or novelties (e.g., ice cream, milk shakes), prepared frozen meals, candy, snack products (e.g., chips), liquid food such as soups, spreads, sauces, salad dressings, prepared meat products, cheese, yogurt and any other fat or oil containing foods, and food ingredients (e.g., wheat flour).

The term food products or foodstuffs also includes functional foods and prepared food products, the latter referring to any pre-packaged food approved for human consumption.

Animal feed including pet food compositions advantageously include food intended to supply necessary dietary requirements, as well as treats (e.g., dog biscuits) or other food supplements. The animal feed comprising the composition according to the invention may be in the form of a dry composition (for example, kibble), semi-moist composition, wet composition, or any mixture thereof. Alternatively or additionally, the animal feed is a supplement, such as a gravy, drinking water, yogurt, powder, suspension, chew, treat (e.g., biscuits) or any other delivery form.

Dietary supplements of the present invention may be delivered in any suitable format. In preferred embodiments, dietary supplements are formulated for oral delivery. The ingredients of the dietary supplement of this invention are contained in acceptable excipients and/or carriers for oral consumption. The actual form of the carrier, and thus, the dietary supplement itself, is not critical. The carrier may be a liquid, gel, gelcap, capsule, powder, solid tablet (coated or non-coated), tea, or the like. The dietary supplement is preferably in the form of a tablet or capsule and most preferably in the form of a hard (shell) gelatin capsule. Suitable excipient and/or carriers include maltodextrin, calcium carbonate, dicalcium phosphate, tricalcium phosphate, microcrystalline cellulose, dextrose, rice flour, magnesium stearate, stearic acid, croscarmellose sodium, sodium starch glycolate, crospovidone, sucrose, vegetable gums, lactose, methylcellulose, povidone, carboxymethylcellulose, corn starch, and the like (including mixtures thereof). Preferred carriers include calcium carbonate, magnesium stearate, maltodextrin, and mixtures thereof. The various ingredients and the excipient and/or carrier are mixed and formed into the desired form using conventional techniques. The tablet or capsule of the present invention may be coated with an enteric coating that dissolves at a pH of about 6.0 to 7.0. A suitable enteric coating that dissolves in the small intestine but not in the stomach is cellulose acetate phthalate. Further details on techniques for formulation for and administration may be found in the latest edition of Remington's Pharmaceutical Sciences (Maack Publishing Co., Easton, Pa.).

In other embodiments, the dietary supplement is provided as a powder or liquid suitable for adding by the consumer to a food or beverage. For example, in some embodiments, the dietary supplement can be administered to an individual in the form of a powder, for instance to be used by mixing into a beverage, or by stirring into a semi-solid food such as a pudding, topping, sauce, puree, cooked cereal, or salad dressing, for instance, or by otherwise adding to a food e.g. enclosed in caps of food or beverage container for release immediately before consumption. The dietary supplement may comprise one or more inert ingredients, especially if it is desirable to limit the number of calories added to the diet by the dietary supplement. For example, the dietary supplement of the present invention may also contain optional ingredients including, for example, herbs, vitamins, minerals, enhancers, colorants, sweeteners, flavorants, inert ingredients, and the like.

In some embodiments, the dietary supplements further comprise vitamins and minerals including, but not limited to, calcium phosphate or acetate, tribasic; potassium phosphate, dibasic; magnesium sulfate or oxide; salt (sodium chloride); potassium chloride or acetate; ascorbic acid; ferric orthophosphate; niacinamide; zinc sulfate or oxide; calcium pantothenate; copper gluconate; riboflavin; beta-carotene; pyridoxine hydrochloride; thiamin mononitrate; folic acid; biotin; chromium chloride or picolonate; potassium iodide; sodium selenate; sodium molybdate; phylloquinone; vitamin D3; cyanocobalamin; sodium selenite; copper sulfate; vitamin A; vitamin C; inositol; potassium iodide. Suitable dosages for vitamins and minerals may be obtained, for example, by consulting the U.S. RDA guidelines.

In other embodiments, the present invention provides nutritional supplements (e.g., energy bars or meal replacement bars or beverages) comprising the composition according to the invention. The nutritional supplement may serve as meal or snack replacement and generally provides nutrient calories. Preferably, the nutritional supplements provide carbohydrates, proteins, and fats in balanced amounts. The nutritional supplement can further comprise carbohydrate, simple, medium chain length, or polysaccharides, or a combination thereof. A simple sugar can be chosen for desirable organoleptic properties. Uncooked cornstarch is one example of a complex carbohydrate. If it is desired that it should maintain its high molecular weight structure, it should be included only in food formulations or portions thereof which are not cooked or heat processed since the heat will break down the complex carbohydrate into simple carbohydrates, wherein simple carbohydrates are mono- or disaccharides. The nutritional supplement contains, in one embodiment, combinations of sources of carbohydrate of three levels of chain length (simple, medium and complex; e.g., sucrose, maltodextrins, and uncooked cornstarch).

Sources of protein to be incorporated into the nutritional supplement of the invention can be any suitable protein utilized in nutritional formulations and can include whey protein, whey protein concentrate, whey powder, egg, soy flour, soy milk soy protein, soy protein isolate, caseinate (e.g., sodium caseinate, sodium calcium caseinate, calcium caseinate, potassium caseinate), animal and vegetable protein and hydrolysates or mixtures thereof. When choosing a protein source, the biological value of the protein should be considered first, with the highest biological values being found in caseinate, whey, lactalbumin, egg albumin and whole egg proteins. In a preferred embodiment, the protein is a combination of whey protein concentrate and calcium caseinate. These proteins have high biological value; that is, they have a high proportion of the essential amino acids. See Modern Nutrition in Health and Disease, eighth edition, Lea & Febiger, publishers, 1986, especially Volume 1, pages 30-32. The nutritional supplement can also contain other ingredients, such as one or a combination of other vitamins, minerals, antioxidants, fiber and other dietary supplements (e.g., protein, amino acids, choline, lecithin, omega-3 fatty acids). Selection of one or several of these ingredients is a matter of formulation, design, consumer preference and end-user. The amounts of these ingredients added to the dietary supplements of this invention are readily known to the skilled artisan. Guidance to such amounts can be provided by the U.S. RDA doses for children and adults. Further vitamins and minerals that can be added include, but are not limited to, calcium phosphate or acetate, tribasic; potassium phosphate, dibasic; magnesium sulfate or oxide; salt (sodium chloride); potassium chloride or acetate; ascorbic acid; ferric orthophosphate; niacinamide; zinc sulfate or oxide; calcium pantothenate; copper gluconate; riboflavin; beta-carotene; pyridoxine hydrochloride; thiamin mononitrate; folic acid; biotin; chromium chloride or picolonate; potassium iodide; sodium selenate; sodium molybdate; phylloquinone; vitamin D3; cyanocobalamin; sodium selenite; copper sulfate; vitamin A; vitamin C; inositol; potassium iodide.

The nutritional supplement can be provided in a variety of forms, and by a variety of production methods. In a preferred embodiment, to manufacture a food bar, the liquid ingredients are cooked; the dry ingredients are added with the liquid ingredients in a mixer and mixed until the dough phase is reached; the dough is put into an extruder, and extruded; the extruded dough is cut into appropriate lengths; and the product is cooled. The bars may contain other nutrients and fillers to enhance taste, in addition to the ingredients specifically listed herein.

It is understood by those of skill in the art that other ingredients can be added to those described herein, for example, fillers, emulsifiers, preservatives, etc. for the processing or manufacture of a nutritional supplement.

Additionally, flavors, coloring agents, spices, nuts and the like may be incorporated into the nutraceutical composition. Flavorings can be in the form of flavored extracts, volatile oils, chocolate flavorings, peanut butter flavoring, cookie crumbs, crisp rice, vanilla or any commercially available flavoring. Examples of useful flavoring include, but are not limited to, pure anise extract, imitation banana extract, imitation cherry extract, chocolate extract, pure lemon extract, pure orange extract, pure peppermint extract, imitation pineapple extract, imitation rum extract, imitation strawberry extract, or pure vanilla extract; or volatile oils, such as balm oil, bay oil, bergamot oil, cedarwood oil, walnut oil, cherry oil, cinnamon oil, clove oil, or peppermint oil; peanut butter, chocolate flavoring, vanilla cookie crumb, butterscotch or toffee. In one embodiment, the dietary supplement contains cocoa or chocolate.

Emulsifiers may be added for stability of the nutraceutical compositions. Examples of suitable emulsifiers include, but are not limited to, lecithin (e.g., from egg or soy), and/or mono- and di-glycerides. Other emulsifiers are readily apparent to the skilled artisan and selection of suitable emulsifier(s) will depend, in part, upon the formulation and final product. Preservatives may also be added to the nutritional supplement to extend product shelf life. Preferably, preservatives such as potassium sorbate, sodium sorbate, potassium benzoate, sodium benzoate or calcium disodium EDTA are used.

In addition to the carbohydrates described above, the nutraceutical composition can contain natural or artificial (preferably low calorie) sweeteners, e.g., saccharides, cyclamates, aspartamine, aspartame, acesulfame K, and/or sorbitol. Such artificial sweeteners can be desirable if the nutritional supplement is intended to be consumed by an overweight or obese individual, or an individual with type II diabetes who is prone to hyperglycemia.

Moreover, a multi-vitamin and mineral supplement may be added to the nutraceutical compositions of the present invention to obtain an adequate amount of an essential nutrient, which is missing in some diets. The multi-vitamin and mineral supplement may also be useful for disease prevention and protection against nutritional losses and deficiencies due to lifestyle patterns.

Examples of fortified food are cereal bars, chewing gum and bakery items, such as cakes and cookies.

Beverages encompass non-alcoholic and alcoholic drinks as well as liquid preparation to be added to drinking water and liquid food. Non-alcoholic drinks are for instance soft drinks, sport drinks, fruit juices, such as for example orange juice, apple juice and grapefruit juice; lemonades, teas, near-water drinks and milk based drinks, such as for example yoghurt drinks. Examples of liquid food include soups and dairy products, for instance yoghurt.

The dosage and ratios of the methoxylated aromatic compound according to the invention with the definitions and preferences as given above or the extract obtainable from *Glycyrrhiza foetida* administered via a nutraceutical composition will, of course, vary depending upon known factors, such as the physiological characteristics of the particular composition and its mode and route of administration; the age, health and weight of the recipient; the nature and extent of the symptoms; the kind of concurrent treatment; the frequency of treatment; and the effect desired which can be determined by the expert in the field with normal trials, or with the usual considerations regarding the formulation of a nutraceutical composition.

In a preferred embodiment, the nutraceutical composition comprises per serving an amount of 0.01 to 1 g, more preferably 0.2 mg to 500 mg of a methoxylated aromatic compound according to the invention with the definitions and preferences as given, preferably in the form an extract obtainable from *Glycyrrhiza foetida*.

In another embodiment a nutraceutical comprises 0.1 mg to 5000 mg, preferably 0.5 to 3000 mg of an extract obtainable from *Glycyrrhiza foetida*.

In another aspect, the invention relates to a composition according to the invention, wherein the composition is a pharmaceutical composition further comprising a pharmaceutically acceptable carrier. In a preferred embodiment the pharmaceutical is in the form of a powder, tablet, capsule, gel, liquid or solid embodiment.

The dosages and ratios of the individual components in a pharmaceutical composition can be determined by the expert in the field with normal preclinical and clinical trials, or with the usual considerations regarding the formulation of pharmaceutical composition.

The pharmaceutical may comprise the composition according to the invention and/or the methoxylated aromatic compound with the definitions and preferences as given above in an amount from preferably 1 mg to 2000 mg per dosage unit, e.g., per capsule or tablet, or from 1 mg per daily dose to 3000 mg per daily dose of a liquid formulation. In a preferred embodiment an extract obtainable from *Glycyrrhiza foetida* is administered via a pharmaceutical composition either in the form of a single dose or by multiple doses in an amount of at least 0.01 mg/kg bodyweight/day, preferably in an amount of 0.1-50 mg/kg body weight/day, most preferably in an amount of 0.3-15 mg/kg body weight/day.

The nutraceutical and pharmaceutical compositions according to the present invention may be in any galenic form that is suitable for administering to the animal body including the human body, more in particular in any form that is conventional for oral administration, e.g. in solid form, for example as (additives/supplements for) food or feed, food or feed premixes, fortified food or feed, tablets, pills, granules, dragées, capsules, and effervescent formulations such as powders and tablets, or in liquid form, for instance in the form of solutions, emulsions or suspensions, for example as beverages, pastes and oily suspensions. The pastes may be filled into hard or soft shell capsules. Examples for other application forms are forms for transdermal, parenteral, topical or injectable administration. The nutraceutical and pharmaceutical compositions may be in the form of controlled (delayed) release formulations. Examples of pharmaceutical compositions also include compositions suitable for topical application and transdermal absorption of the phenolic compound, such as crèmes, gels, sprays, dry sticks, powders etc.

A person skilled in the art knows which carriers can be used as pharmaceutically acceptable carriers. Examples of such pharmaceutically acceptable carriers are both inorganic and organic carrier materials, suitable for oral/parenteral/injectable administration and include water, gelatin, gum arabic, lactose, starch, magnesium stearate, talc, vegetable oils, and the like.

Besides a methoxylated aromatic compound with the definitions and preferences as given above and a pharmaceutically acceptable carrier, the pharmaceutical composition according to the present invention, may further comprise conventional pharmaceutical additives and adjuvants, excipients or diluents, including, but not limited to, water, gelatin of any origin, vegetable gums, ligninsulfonate, talc, sugars, starch, gum Arabic, vegetable oils, polyalkylene glycols, flavoring agents, preservatives, stabilizers, emulsifying agents, buffers, lubricants, colorants, wetting agents, fillers, and the like.

The methoxylated aromatic compounds according to the invention may be used in combination with other nutraceutical compositions or therapeutic agents know to those skilled in the art for treatment or prevention of inflammatory disorder by administration prior to, simultaneously with or following the administration of the methoxylated aromatic compound.

In another embodiment of the invention, the compositions of the invention and/or the methoxylated aromatic compound according to the invention with the preferences and definitions as given above may be incorporated into cosmetic or dermatological compositions (the latter compositions are a specific type of pharmaceutical compositions) such as skin care preparations for the treatment, co-treatment or prevention of inflammation of the skin such as for the treatment, co-treatment or prevention of impure skin. Examples of impure skin include pimples, acne and other skin impurities with an inflammatory aspect.

Therefore, the invention also relates to compositions according to the invention which are cosmetic compositions. In another embodiment the invention relates to the use of the cosmetic composition for the cosmetic treatment, co-treatment or prevention of inflammation of the skin, in particular for the cosmetic treatment, co-treatment or prevention of impure skin. The invention also relates to the use of the methoxylated aromatic compound or a composition according to the invention for the manufacture of a dermatological composition for the treatment, co-treatment or prevention of inflammation of the skin, in particular impure skin. Also, the invention relates to a method for the treatment, co-treatment or prevention of inflammation of the skin, in particular of impure skin such as for example acne, said method comprising the step of administering an effective amount of the dermatological composition according to the invention to humans, which are in need thereof. Also, the invention relates to a method for cosmetic treatment, co-treatment or prevention of inflammation of the skin of impure skin by a cosmetic composition according to the invention.

The cosmetic or dermatological compositions according to the invention may be in the form of a suspension or dispersion in solvents or fatty substances, or alternatively in the form of an emulsion or micro emulsion (in particular of O/W or W/O type, O/W/O or W/O/W-type, wherein O stands for organic phase and wherein W stands for water phase), such as a cream, a paste, a lotion, a thickened lotion or a milk, a vesicular dispersion in the form of an ointment, a gel, a solid tube stick or an aerosol mousse, and may be provided in the form of a mousse, foam or a spray foams, sprays, sticks or aerosols or wipes. Examples of cosmetic or dermatological compositions are skin care preparations, in particular, body oils, body lotions, body gels, treatment creams, skin protection ointments, moisturizing gels, moisturizing sprays, revitalizing body sprays, after sun preparations or sunscreen formulations.

The cosmetic or dermatological composition for the treatment, co-treatment or prevention of inflammation of the skin, such as for example impure skin may be in a form that is conventional for oral administration, examples of which are described above and also include beauty foods and supplements.

The cosmetic or dermatological compositions of the invention may further comprise the usual cosmetic respectively dermatological adjuvants and/or additives such as preservatives/antioxidants, fatty substances/oils, water, organic solvents, silicones, thickeners, softeners, emulsifiers, additional light screening agents, antifoaming agents, moisturizers, fragrances, surfactants, fillers, sequestering agents, anionic, cationic, nonionic or amphoteric polymers or mixtures thereof, propellants, acidifying or basifying agents, dyes, colorants, pigments or nanopigments, light stabilizers, insect repellants, skin tanning agents, skin whitening agents, antibacterial agents, preservatives active ingredients or any other ingredients usually formulated into cosmetics.

Active ingredients which may be included in the cosmetic or dermatological compositions of the invention are for example vitamins and derivatives thereof, for example tocopherol, tocopherolacetate, ascorbic acid, ascorbyl phosphate, vitamin Q, D, and K, retinol, retinal, retinoic acid, retinol acetate, retinol palmitate, biotin, carotinoid derivatives such as beta carotene, lycopene, asthaxanthin, vegetable extracts, antibacterial ingredients, instable amino acids comprising dipeptides, oligopeptides and polypeptides such as methionine, cysteine, cystine, tryptophan, phenylalanine, tyrosine, phenols, polyphenols or flavanoids, bisabolol, allantoin, phytantriol, panthenol, AHA acids, ubiquinones such as Coenzym Q 10, ceramides, pseudoceramides, essential oils, plant extracts deoxyribonucleic acid.

The necessary amounts of the cosmetic and dermatological adjuvants, additives and/or additional active ingredients can, based on the desired product, easily be chosen by a person skilled in the art and will be illustrated in the examples, without being limited hereto.

In yet another aspect, the invention also relates to a composition of the invention, wherein the composition is a cosmetic or dermatological composition comprising a cosmetic respectively dermatological adjuvant and/or a cosmetic respectively dermatological additive and/or a cosmetic respectively dermatological additional active ingredient.

The cosmetic or dermatological compositions comprise the methoxylated aromatic compound in an effective amount. The term "effective amount" is preferably at least 0.01% by weight of the composition. Preferably, the compositions comprise the methoxylated aromatic compound in an amount between 0.01 wt.-% and 20 wt.-%, more preferably between 0.05 and 10 wt.-%, still more preferably between 0.1 and 5 wt.-%.

The invention will now be elucidated by way of the following examples, without however being limited thereto.

EXAMPLE 1

Soft Gelatin Capsule

Soft gelatin capsules are prepared by conventional procedures providing a dose of methoxylated aromatic compound of 10 mg. A suitable daily dose is 1 to 5 capsules.
Other ingredients: glycerol. Water, gelatine, vegetable oil

EXAMPLE 2

Hard Gelatin Capsule

Hard gelatin capsules are prepared by conventional procedures providing a dose of methoxylated aromatic compound of 20 mg. A suitable daily dose is 1 to 5 capsules.
Other Ingredients:
Fillers: lactose or cellulose or cellulose derivatives q.s.
Lubricant: magnesium stearate if necessary (0.5%)

EXAMPLE 3

Tablet

Tablets are prepared by conventional procedures providing as active ingredient 20 mg of methoxylated aromatic compound per tablet, and as excipients microcrystalline cellulose, silicone dioxide ($SiO_2$), magnesium stearate, crospovidone NF (which is a disintegration agent) ad 500 mg.

EXAMPLE 4

Soft Drink

A soft drink containing a methoxylated aromatic compound may be prepared as follows:

A soft drink is prepared from the following ingredients:

| ingredient | [g] |
|---|---|
| A. juice concentrates and water soluble flavours | |
| 60.3°Brix, 5.15% acidity | 657.99 |
| 43.5° Brix, 32.7% acidity | 95.96 |
| Orange flavour, water soluble | 3.43 |
| Apricot flavour, water soluble | 6.71 |
| water | 26.46 |
| B. color | |
| â-carotene 10% CWS | 0.89 |
| water | 67.65 |
| C. Acid and antioxidant | |
| Ascorbic acid | 4.11 |
| Citric acid anhydrous | 0.69 |
| Water | 43.18 |
| D. stabilizers | |
| pectin | 0.20 |
| Sodium benzoate | 2.74 |
| water | 65.60 |
| E. oil soluble flavours | |
| Orange flavour, oil soluble | 0.34 |
| Orange oil distilled | 0.34 |
| F. active ingredient | |
| Methoxylated aromatic compound | Amount providing 500 mg |

Fruit juice concentrates and water soluble flavours are mixed without incorporation of air. The color is dissolved in deionized water. Ascorbic acid and citric acid are dissolved in water. Sodium benzoate is dissolved in water. The pectin is added under stirring and dissolved while boiling. The solution is cooled down. Orange oil and oil soluble flavours are premixed. The active ingredient as mentioned under F is stirred into the fruit juice concentrate mixture of A.

In order to prepare the soft drinks all components A-F are mixed together before homogenizing using a Turrax and then a high-pressure homogenizer ($p_1$=200 bar, $p_2$=50 bar).

EXAMPLE 5

Inhibition of the Production of Inflammatory Mediators

The anti-inflammatory effects of structurally related compounds isolated from *Glycyrrhiza foetida* like Amorfrutin A (III), Amorfrutin B (II), cannabigerolic acid monomethyl ether and 2-hydroxy-4-methoxy-3-(3-methyl-2-butenyl)-6-pentyl-benzoic acid as well as two new structures (2-hydroxy-4-methoxy-3-(2-hydroxy-3-methyl-3-butenyl)-6-(2-phenylethyl)-benzoic acid (I), 2-hydroxy-4-methoxy-3-(2-hydroxy-3-methyl-3-butenyl)-6-pentyl-benzoic acid (VI) were determined in cellular assays.

The compounds were isolated from an extract of *Glycyrrhiza foetida* by extraction of the dried plant material with methanol:MTB (9:1). Extracts were obtained from different part of the plant. The thus obtained crude extract was fractionated by preparative HPLC in a buffered solvent system. Biological activities of the extracts were tested in cellular systems as described below for isolated compounds.

Pure compounds were assayed in vitro in cellular systems. The inhibition of the synthesis of pro-inflammatory prostaglandins (PG) and of nitric oxide by the extracts or compounds was measured. $PGE_2$ plays a critical role in the inflammation process, while nitric oxide (NO) is a hallmark of inflammation in various chronic inflammatory diseases including various forms of arthritis, gastrointestinal diseases and metabolic syndrome X.

The effects of extracts or compounds on the inflammatory response were tested in cellular assays using a murine macrophage indicator cell line, RAW264.7. The cells were purchased from ATCC (Manassas, Va., USA) and cultured in DMEM containing streptomycin/penicillin, non-essential amino acids and 10% fetal calf serum (FCS). In order to test a large range of concentration of compounds, cells (~50'000/well) were seeded into flat-bottomed microtiter plates and cultured for one day. Cells were then starved in complete medium containing 0.25% FCS (D-025). After overnight culture, medium was removed and replaced by 100 μL of D-025 containing the test compounds at twice the final concentration. Subsequently, 100 μL of D-025 containing 2 μg/ml LPS was added (i.e. final LPS concentration of 1 μg/ml) and the cells cultured for 24 hours.

Compounds were usually tested in a concentration range from 0.2 to 50 μM in two-fold dilution steps. Extracts were tested in a range from 0.2-50 mg/L. All treatments were done in duplicates and several experimental series were done for each treatment. Concentrations of nitrite, which was rapidly formed from nitric oxide released by cells, were determined by the Griess reaction using sodium nitrite as standard. Briefly, 50 μl of supernatant was mixed with Griess reagent 1 (25 μL) and Griess reagent 2 (25 μL), centrifuged and the optical density at 540 nm determined. $PGE_2$ secreted into the cell culture medium was determined by EIA obtained from Cayman Chemicals (Ann Harbor, Wis., USA) and used according to the manufacturer's instructions. All determinations were done in duplicates and at various dilutions of the culture supernatant. $IC_{50}$ values were calculated using a two-parametric least-square fitting equation $[y=A+((B-A)/(1+((C-x)\hat{\,}D))]$ for best-fit curves (Excel fit software program).

The effects of compounds on inhibition of two inflammatory parameters are given in the Tables below. Extracts obtained from different parts of the plant have strong although divergent anti-inflammatory properties. Six compounds identified in *Glycyrrhiza foetida* extracts (e.g. Amorfrutin A (III), B, Cannabigerolic acid monomethyl ether) potently reduced the production of nitric oxide (NO) with an $IC_{50}$ of <~20 μmol/L and most of the tested compound also reduced the $PGE_2$ production in the tested concentration range. Collectively, the data provide evidence that the below-mentioned compounds isolated from *Glycyrrhiza foetida* modulate inflammatory reactions in vitro.

TABLE

| $IC_{50}$ values for extracts obtained from different parts of the plant | | |
|---|---|---|
| Plant material | $IC_{50}$ Nitric Oxide | $IC_{50}$ $PGE_2$ |
| leaves | 2.4 ± 0.4 mg/L | 3.8 ± 0.6 mg/L |
| stems | 10.8 ± 6.3 mg/L | >50 mg/L |
| fruits | 4.2 ± 1.9 mg/L | 2.2 ± 0.6 mg/L |
| flowers | 2.1 ± 0.4 mg/L | 2.1 ± 0.5 mg/L |

TABLE

IC$_{50}$ values for single compounds listed in decreasing effect on nitric oxide production

| Compound | IC$_{50}$ Nitric Oxide | IC$_{50}$ PGE$_2$ |
|---|---|---|
| Amorfrutin A (III) | 7.1 ± 0.1 μmol/L | 74.1 ± 12.1 μmol/L |
| 2-hydroxy-4-methoxy-3-(3-methyl-2-butenyl)-6-pentyl-benzoic acid | 10.9 ± 1.2 μmol/L | >50 μmol/L |
| 2-hydroxy-4-methoxy-3-(2-hydroxy-3-methyl-3-butenyl)-6-(2-phenylethyl)-benzoic acid (I) | 14.6 ± 0.3 μmol/L | 40.7 ± 11.8 μmol/L |
| Amorfrutin B (II) | 22.8 ± 4.1 μmol/L | >100 μmol/L |
| 2-hydroxy-4-methoxy-3-(2-hydroxy-3-methyl-3-butenyl)-6-pentyl-benzoic acid (VI) | 22.1 ± 1.6 μmol/L | 18.9 ± 1.6 μmol/L |
| Cannabigerolic acid monomethyl ether | 31.3 ± 2.5 μmol/L | 17.9 ± 11.6 μmol/L |

EXAMPLE 6

Modulation of the Expression Levels of Inflammatory Genes

The effect of the compounds has also been evaluated on the level of the expression of genes that are involved in the inflammatory response. These comprise genes of the prostaglandin synthesis pathway, cytokines and chemokines or inducible nitric oxide synthase (iNOS). RAW 264.7 cells were stimulated in the presence of different concentrations of substances. After 4 hours, RNA was extracted and the expression of genes determined by quantitative RT-PCR as described (Richard, N., Porath, D., Radspieler, A. and Schwager, J. Effects of resveratrol, piceatannol, tri-acetoxystilbene, and genistein on the inflammatory response of human peripheral blood leukocytes. *Mol Nutr Food Res* 2005. 49: 431-442). As an example, data are shown for amorfrutin A, that significantly reduced e.g. inducible nitric oxide synthase (iNOS), interleukin-10 (IL-10) or matrix metalloproteinase 9 (MMP-9). Collectively, the results reveal significant effects of the compounds on the expression of distinct genes involved in the inflammatory response.

TABLE

Effect of Amorfrutin A on the expression of some inflammatory genes. The level of mRNA for a given gene is expressed relative to the level observed in cells that were stimulated with LPS only (=100%). Values lower than 100% indicate that the substance had an inhibitory effect on the expression of the relevant gene.

| Gene | % expression in the presence of 25 μM/L Amorfrutin A |
|---|---|
| iNOS | 52 |
| IL-10 | 22 |
| MMP-9 | 69 |
| IL-1 alpha | 94 |

EXAMPLE 7

Effect of *Glycyrrhiza foetida* Extract on Carrageenan-Induced Paw Edema in Rats The anti-inflammatory activity of a *Glycyrrhiza foetida* extract was evaluated in vivo in the carrageenan-induced paw edema model. This model has long been used to assess the anti-inflammatory properties of agents that inhibit prostaglandins, such as nonsteroidal anti-inflammatory drugs (NSAIDs). The model causes time-dependent edema formation following carrageenan administration into the subplantar surface of a rat paw.

Twenty male Wistar (Han) rats weighing 120 to 150 g were randomized in two groups. They were housed in a temperature (21±3° C.) and relative humidity (30-80%) controlled room with a 12-h light/dark cycle. They had ad libitum access to filtered tap-water and standard pelleted laboratory chow throughout the study and were housed 4 to 5 per cage and at least a 5 day acclimatization period was observed before any testing.

*Glycyrrhiza foetida* extract (100 mg/kg) suspended in 1% methylcellulose/1% ethanol/3% Tween 80 (in a volume of 5 mL/kg) or vehicle alone were administered by the oral route in a coded and random order after an overnight fast. Thirty minutes later, inflammation is induced by subplantar injection of 0.05 ml of a 1.5% carrageenan suspension into the right hindpaw. The left hindpaw was injected with 0.05 ml physiological saline. The paw volume of each rat was measured in mL at two time points once 1.5 h and once 3.5 h after the injection of carrageenan. The right paw edema volume is determined by the difference between the right hindpaw volume (inflamed paw) and the left (non-inflamed) hindpaw volume. The anti-inflammatory effect on edema volume in treated-groups was expressed as percent (%) inhibition [(mean of vehicle-treated group paw edema volume−mean of the treated group paw edema volume)/mean of vehicle-treated group paw edema volume)×100].

TABLE 1

Pharmacological effects of *Glycyrrhiza foetida* extract after oral administration on carrageenan-induced paw edema in rats

| | Paw edema volume (ml) | | |
|---|---|---|---|
| Time (hours) | vehicle-treated animals | *Glycyrrhiza foetida* treated animals | % Inhibition of *Glycyrrhiza foetida* |
| 1.5 | 0.60 | 0.47 | 22 |
| 3 | 0.73 | 0.52 | 29 |

All data of paw edema volume are expressed in mL as Mean of 10 rats in each group. % inhibition vs vehicle-treated group is calculated.

It is shown that *Glycyrrhiza foetida* extract (100 mg/kg) inhibited the mean paw edema volume 1.5 h and 3.5 h after the carrageenan injection as compared to the control group treated with the vehicle. Therefore, *Glycyrrhiza foetida* extract has anti-inflammatory action in mammals.

EXAMPLE 7

Anti-Acne Treatment

| Phase | INCI Nomenclature | wt. % |
| --- | --- | --- |
| 1 | Glyceryl Myristate | 1.50 |
|   | Cetyl Alcohol | 1.50 |
|   | C12-15 Alkyl Benzoate | 4.00 |
|   | Phenoxyethanol & Methylparaben & Ethylparaben & Butylparaben & Propylparaben & Isobutylparaben | 0.80 |
|   | Isononyl Isononanoate | 2.00 |
|   | Steareth-2 | 1.50 |
|   | Steareth-21 | 1.50 |
| 2 | Butylene Glycol | 2.00 |
|   | Glycerin | 3.00 |
|   | Disodium EDTA | 0.10 |
|   | Xanthan Gum | 0.30 |
|   | Arcylates/C10-30 Alkyl Acrylate Crosspolymer | 0.25 |
|   | Aqua (e.g. deionized water) | Ad 100 |
| 3 | Aqua (e.g. deionized water) | 10.00 |
|   | Sodium Metabisulfite | 0.05 |
| 4 | Methoxylated aromatic compound according to the invention | 0.60 |

Procedure: Heat part 1 up to 85° C.; and heat also part 2 up to 85° C. When both have the same temperature add part 2 to part 1 while homogenizing intensively. Cool down the product to 35° C. while stirring. Now add part 3 and 4 homogenize intensively again. It is generally recommended to use vacuum while producing the emulsion.

The invention claimed is:

1. A method for treatment or co-treatment of osteoarthritis and/or rheumatoid arthritis in animals including humans said method comprising the step of administering an effective amount of an Amorfrutin A to animals including humans, which are in need thereof.

2. A method according to claim 1 wherein the Amorfrutin A is present in an extract of *Glycyrrhiza foetida*.

3. A method according to claim 2 wherein the extract is present in a food or nutraceutical.

4. A method according to claim 2 wherein the extract is a methanol extract.

5. A method according to claim 1 wherein the Amorfrutin A is in an amount of from 0.5 mg/day to 2000 mg/day.

6. A method according to claim 1 wherein the Amorfrutin A is in an amount of from 5 mg/day to 500 mg/day.

7. A method according to claim 1, wherein the animal is not human.

8. A method of reducing symptoms associated with osteoarthritis and/or rheumatoid arthritis selected from the group consisting of: reducing joint inflammation, maintaining joint health, preventing joint stiffness, increasing mobility, providing supple joint, providing flexible joints, providing joint lubrication, relieving pain due to arthritis, relieving pain associated with joint inflammation, and decreasing joint swelling,
comprising administering an effective amount of Amorfrutin A to an animal.

9. A method according to claim 8 wherein the Amorfrutin A is present in an extract of *Glycyrrhiza foetida*.

10. A method according to claim 9 wherein the extract is present in a food or nutraceutical.

11. A method according to claim 9 wherein the extract is a methanol extract.

12. A method according to claim 8 wherein the Amorfrutin A is in an amount of from 0.5 mg/day to 2000 mg/day.

13. A method according to claim 8 wherein the Amorfrutin A is in an amount of from 5 mg/day to 500 mg/day.

14. A method according to claim 8 wherein the animal is not human.

* * * * *